United States Patent
Gordon et al.

[19]

[11] Patent Number: 6,146,421
[45] Date of Patent: Nov. 14, 2000

[54] MULTIPLE AXIS INTERVERTEBRAL PROSTHESIS

[75] Inventors: Dennis P. Gordon, Las Vegas, Nev.; William E. Maya, San Clemente; Rick D. Roberts, McKinleyville, both of Calif.; James C. Thomas, Jr., Las Vegas, Nev.

[73] Assignee: Gordon, Maya, Roberts and Thomas, Number 1, LLC, McKinleyville, Calif.

[21] Appl. No.: 09/233,566

[22] Filed: Jan. 19, 1999

Related U.S. Application Data

[63] Continuation-in-part of application No. 09/128,756, Aug. 4, 1998.
[60] Provisional application No. 60/054,622, Aug. 4, 1997.

[51] Int. Cl.[7] .................................................. A61F 2/44
[52] U.S. Cl. ............................................... 623/17.15
[58] Field of Search .......................... 623/17.11, 17.16; 606/61

[56] References Cited

U.S. PATENT DOCUMENTS

| | | | |
|---|---|---|---|
| 5,258,031 | 11/1993 | Salib et al. ................................. | 623/17 |
| 5,314,477 | 5/1994 | Marnay ...................................... | 623/17 |
| 5,360,430 | 11/1994 | Lin ............................................ | 606/61 |
| 5,401,269 | 3/1995 | Büttner-Janz et al. .................... | 623/17 |
| 5,425,773 | 6/1995 | Boyd et al. ................................. | 623/17 |
| 5,507,816 | 4/1996 | Bullivant .................................... | 623/17 |
| 5,562,738 | 10/1996 | Boyd et al. ................................. | 623/17 |
| 5,645,596 | 7/1997 | Kim et al. .................................. | 623/17 |
| 5,674,296 | 10/1997 | Bryan et al. ............................... | 623/17 |
| 5,676,701 | 10/1997 | Yuan et al. ................................. | 623/17 |
| 5,683,465 | 11/1997 | Shinn et al. ............................... | 623/17 |

FOREIGN PATENT DOCUMENTS

WO91/13598  9/1991  WIPO ............................... A61F 2/44

*Primary Examiner*—Michael J. Milano
*Attorney, Agent, or Firm*—Christie, Parker & Hale, LLP

[57] ABSTRACT

The present invention relates to an intervertebral prosthetic disk. The prosthesis includes a male component with a support plate, an attachment element allowing fixation to a vertebra, and an articulating projection defining a concave lower surface. The prosthesis also includes a female component with a support plate, an attachment element allowing fixation to a vertebra, and a circular pocket with a flat bottom and angled walls suitable for receiving the articulating projection. A generally hemispheric bearing is provided between the male and female components. The hemispheric bearing includes an upper convex surface for cooperating with the concave lower surface of the articulating projection of the male component and a flat lower surface for cooperating with the flat bottom surface of the circular pocket of the female component. The male component is placed inside the female component with the hemispheric bearing between the two components and the male and female components are attached to adjacent vertebrae and act as a replacement for a disk. The prosthesis allows for a natural range of motion for the patient.

22 Claims, 6 Drawing Sheets

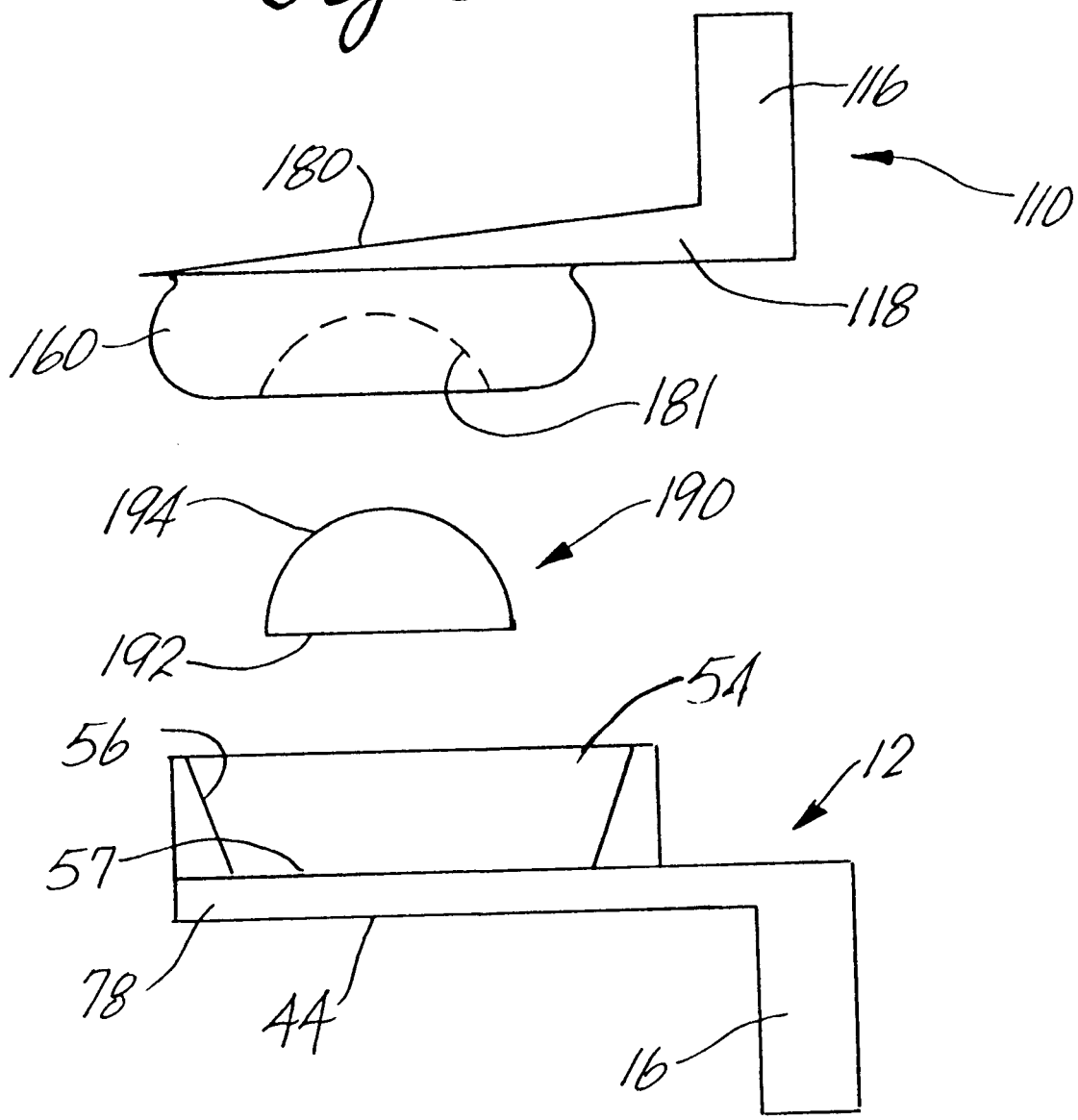

MULTIPLE AXIS INTERVERTEBRAL PROSTHESIS

CROSS-REFERENCE TO RELATED APPLICATIONS

This application is a continuation in part of U.S. patent application Ser. No. 09/128,756, filed Aug. 4, 1998 which claims the priority of U.S. Provisional Patent Application No. 60/054,622, filed Aug. 4, 1997.

FIELD OF THE INVENTION

The present invention relates to an intervertebral prosthesis for the replacement of multiply-operated or degenerative disks that are creating painful motion or nerve root compression. In particular, this invention relates to an articulating self-centering disk prosthesis.

BACKGROUND OF THE INVENTION

Disk disease is endemic. When a spinal disk in a patient is no longer serviceable, a fusion is often done. A fusion involves the removal of the degenerative vertebral disk, which had allowed for movement and rotation of the adjacent vertebrae relative to one another. The two vertebrae surrounding the disk are then joined and fixed, removing the mobility from that area. However, fusions have many disadvantages. They are destructive and have a significant failure rate. They encourage degenerative disease of the disks above and below and most often require donor bone, which causes its own set of complications.

The evolution of surgical treatment of other diseased joints has progressed from fusion, to debridement and resurfacing and then to joint replacement. The standard of care for surgical treatment of advanced disease of hip and knee joints is now joint replacement. However, the search for a working spinal disk replacement has not yielded as great of a success as of yet. The currently available experimental prostheses are not widely accepted.

There are a number of ball and socket type arrangements that have been developed for disk prostheses, but the problem with existing prostheses is that none of the devices address the need for self centering of the ball within the socket. Self-centering is an important feature because it allows the prosthesis to imitate the normal motion of the disk. The availability of a mechanism which enables a ball and socket type prosthesis to self-center would give a patient a flexible, natural-feeling prosthesis. An additional problem which is not addressed by the existing devices is any sort of specific method for building lordosis into the prosthesis. The advantage of building lordosis into the prosthesis is that it allows the back to have a more natural curvature, rather than an artificial stiffness. For a disk prosthesis to be as successful as some other joint replacements, it needs to allow for as much natural movement as possible.

It is also important that a prosthesis allows the anatomy of the motion segment to be the constraining factor for the limits of motion. If the prosthesis is intrinsically constrained, then it must bear the stresses of constraint, particularly at the bone/prosthesis interface, as well as internally in the prosthesis. Other fully constrained protheses, such as total knees or elbows, have failed. If a prosthesis was developed that allowed the anatomy of the motion segment to be the constraining factor, then the facets and soft tissue would bear the stresses of constraint allowing for longer life of the prosthesis. The life of the prosthesis should be long enough to make the operation worthwhile, so it need not be repetitive.

It is desirable that a prosthesis be provided that allows for a significant range of motion, that mimics the motion of an actual vertebral disk. Ideally, it would be stable, without intrinsic constraining factors, but not stiff, so it will have a long lifetime, and feel as natural as possible.

SUMMARY OF THE INVENTION

Therefore, the present invention provides for an intervertebral prosthesis that self-centers, allows a range of motion, and in a preferred embodiment also provides for lordosis considerations. The prosthesis is designed to alleviate a painful motion segment, for degenerative disk disease, for the multiply operated disk, or to relieve nerve root compression.

The prosthesis assembly comprises a male component, a female component and an optional generally hemispheric bearing. The male component consists of an upper support plate, preferably wedge shaped, from which, in a particularly preferred embodiment, a flange extends. The flange preferably defines a mounting tab that extends vertically from the edge of the component. The mounting flange includes a plurality of holes through which one or more attachment elements, such as a screw, may pass, for fixation of the male component to a vertebra. The hole is preferably shaped as a figure eight. The preferred means for attachment to the adjacent vertebra is a plurality of screws which pass through a plurality of holes in the flange. The male component also consists of a doughnut shaped projection which, in an optional but particularly preferred embodiment, includes a generally a hemispheric void.

The female component consists of a lower support plate, preferably flat, from which a flange extends vertically to define a mounting tab similar to that of the male component. As with the male component, the preferred means for attaching the female portion to the adjacent vertebra is a plurality of screws which pass through holes in the flange. The female component also defines a circular pocket with angled walls and a flat floor.

The optionally provided hemispheric bearing has a hemispherically shaped upper bearing surface and a flat lower bearing surface. The upper bearing surface engages the hemispheric void of the male component while the flat lower bearing surface engages the flat floor of the circular pocket of the female component. The angled walls of the circular pocket of the female component provide a surface upon which the projection of the male component can rest. The doughnut shaped projection preferably contains a double radius for ease in self-centering. Assembled as described, the upper and lower plates are able to articulate with respect to one another. The range of movement is generally provided by the projection of the male component sliding against the angled walls of the pocket of the female component. The hemispheric bearing helps to distribute stress from the projection of the male component to the floor of the pocket so that the walls of the pocket of the female component do not bear the entire stress. It should be noted that the flat lower surface of the hemispheric bearing is permitted to slide freely within the pocket of the female component so as to provide various centers of rotation and permit the device to both articulate, yet be self-centering.

In a preferred embodiment, the female component has a coating or insert on the inside surface of the pocket to reduce friction between the components. Preferably, the material for the coating is plastic or ceramic. The hemispheric bearing may similarly be coated with a friction reducing material.

In a preferred embodiment, the upper and lower plates include a porous coating on the bone-facing surfaces. By including a porous coating, bone growth will further help to anchor the support plates to the vertebrae. The components are preferably made of a metal alloy or ceramic material. The components may also be made of dissimilar materials from one another. A particularly preferred prosthesis is made of chromium cobalt alloy to give strength and longevity to the prosthesis.

DESCRIPTION OF THE DRAWINGS

These and other features and advantages of the invention will be more fully understood when considered with respect to the following detailed description, claims and accompanying drawings where:

FIG. 6 is an exploded side view partially in section of an alternate embodiment of the invention including a hemispheric bearing.

DETAILED DESCRIPTION

Figure 1:
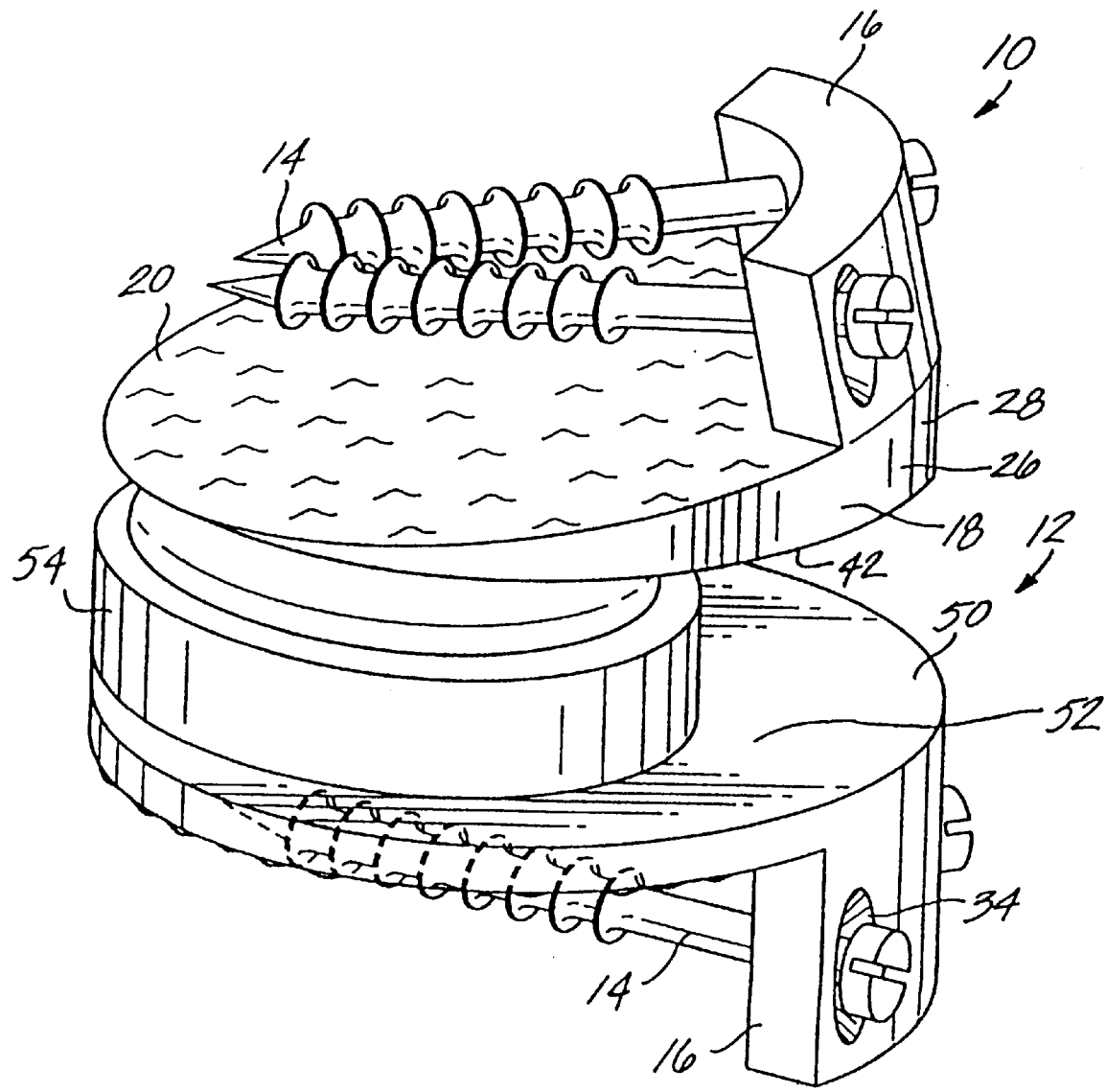
FIG. 1 is a perspective view of an intervertebral prosthesis, according to the present invention with the two components placed together.
Figure 4:
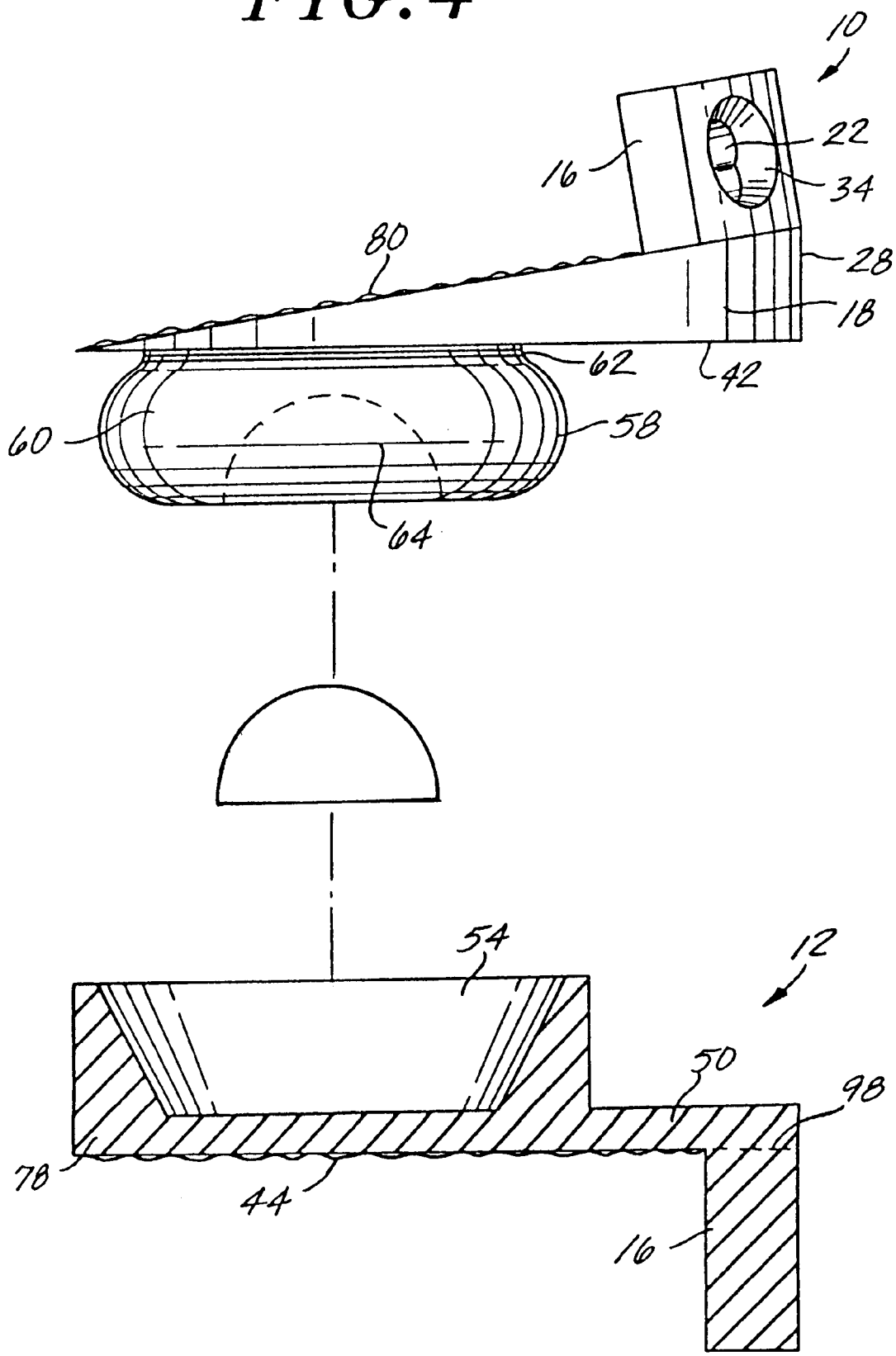
FIG. 4 is a side view, partly in section of the male component and the female component of the intervertebral prosthesis of FIG. 1 spaced apart from one another.

The present invention relates to a variable axis intervertebral disk prosthesis (see FIG. 1). The prosthesis has two components (see FIG. 4), male 10 and female 12, and is for implantation between two adjacent vertebrae in place of a spinal disk. Attachment to the adjacent vertebrae is accomplished at least in part by means of an attachment element, preferably mechanical attachment elements such as screws 14 which pass through a flange 16. Alternatives to screws such as pegs or posts are acceptable means for attaching the components to the vertebrae, as long as they are strong enough to handle the compressive forces exerted on it, and are a reliable form of fixation. Bone cement may also be used for attachment to the adjacent vertebrae, either in place of or in addition to mechanical attachment elements. The preferred length and diameter of the mechanical attachment elements is determined by the surgeon depending on the size of the patient and the location in the spine where the disk is being replaced. If using screws, they may be inserted straight into the vertebrae or at an angle. In one preferred embodiment, the screws are inserted straight into the vertebrae (see FIG. 1). In another preferred embodiment, a screw is inserted into the vertebra at an angle (see FIG. 5).

The male portion 10 of the prosthesis comprises a cylindrical support plate 18, which in a preferred embodiment is wedge shaped. The wedge shaped plate 18 allows for building lordosis into the prosthesis. The wedge shaped plate 18 has one rough-faced surface 20 that would mate with a vertebra. In a preferred embodiment, the male component 10 is the upper component and the rough surface 20 is on the upper surface 80 of the wedge shaped plate 18 (see FIG. 4). The rough surface allows for another means of fixation to a vertebra, as an alternative to or in addition to the mechanical attachment elements. A presently preferred embodiment has both attachment elements, such as screws 14, and a rough surface 20 to provide for the most stable fixation.

Figure 3:
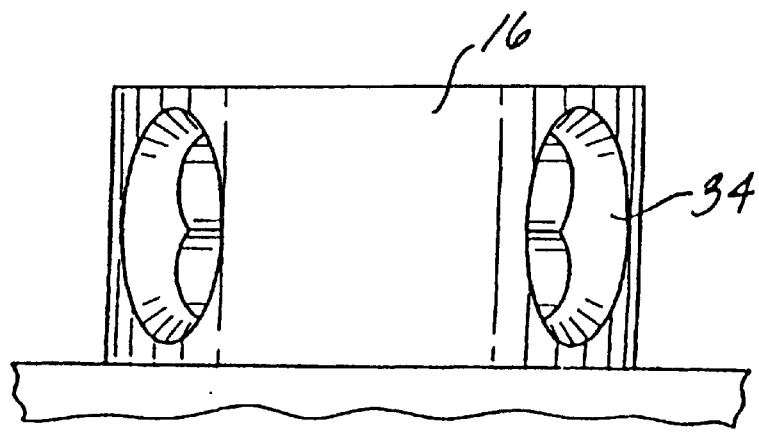
FIG. 3 is a perspective view of a flange portion of the intervertebral prosthesis of FIG. 1 with figure-eight shaped attachment openings.

Extending vertically from the edge of the upper surface 20 of the support plate is at least one flange 16. In a preferred embodiment, the male component is the upper component and the flange extends upward from the thick side of the wedge shaped plate 28 (see FIG. 1). The flange is a mounting tab that can receive the attachment elements, such as screws 14. The screws are guided through openings 22 in the flange in order to attach the male portion 10 to a vertebra. There are at least two openings 22 through which (at least two) attachment elements can pass. In a preferred embodiment, the openings 22 in the flange 16 are figure eight shaped openings 34 (see FIG. 3). The figure eight shaped opening aids in facilitating different screw heights. Different heights are chosen by the surgeon depending on what best fits each particular patient. The opening 22 can also be circular, or oval in shape.

Figure 2:
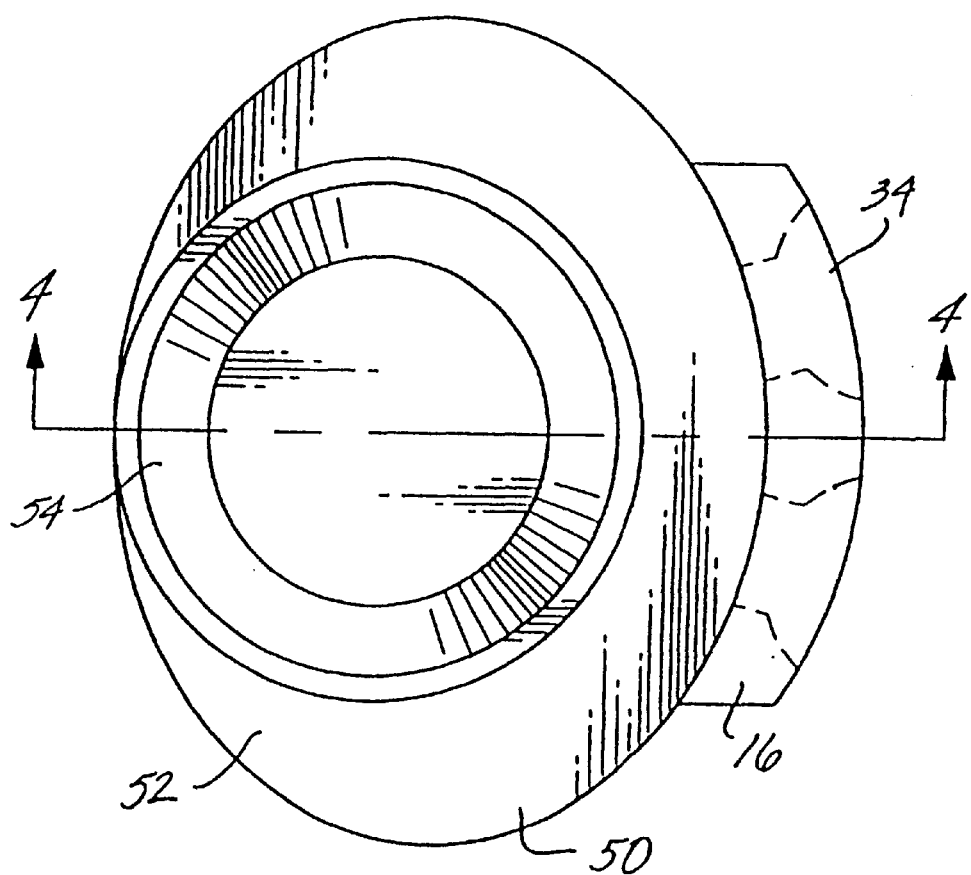
FIG. 2 is a top view of the female component of the intervertebral prosthesis of FIG.I.

The openings can also have a wider mouth section at their outer edge (see FIG. 2) to accept the heads of screws placed through the openings. For ease in seeing the mouth sections, the screws in FIG. 1 are backed slightly out of the openings. However, when fully inserted, the heads of the screws would be a least partly received within the mouth sections to present a smoother outer surface for the flange, thereby causing less irritation to overlying tissue.

Figure 5:
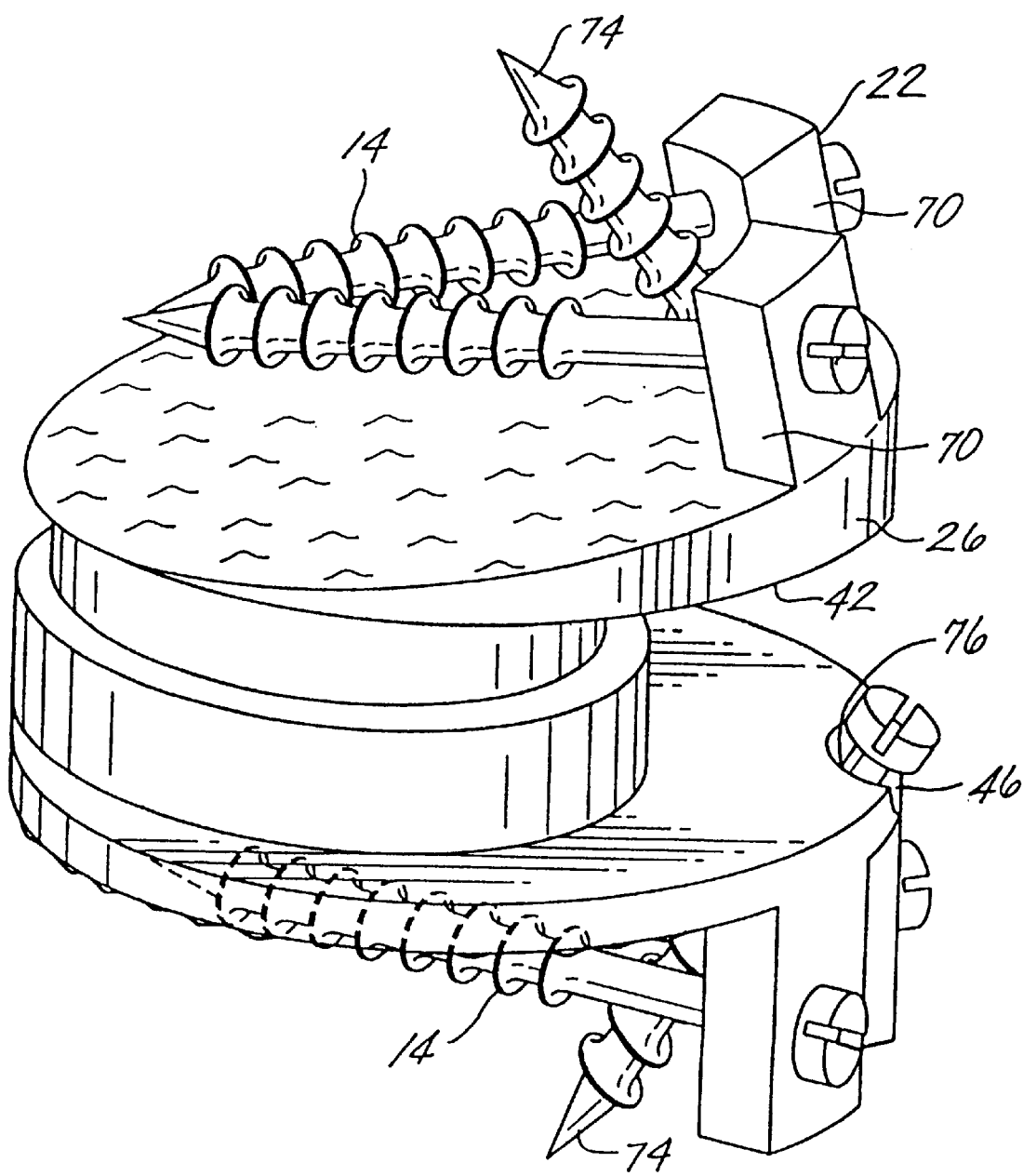
FIG. 5 is a perspective view of an alternate embodiment showing a double flange with an angled screw.

In another embodiment, there are two flanges 70 extending vertically from the plate (see FIG. 5). Each flange has at least one opening 22 for an attachment element to pass through.

In an alternative embodiment, the male component has an additional opening 24 for attachment to a vertebra (see FIG. 5). This opening 24 extends from the lower edge of the cylindrical wedge 26 on the male portion 10 at the thick side of the wedge 28. The opening 24 is angled so that an attachment element, such as a screw 74, can be inserted into the vertebra through the opening 24 at an angle. The opening is also recessed at the lower end 36, to receive the head of a screw 30 which is at an angle.

The male component further comprises a projection with an articulating surface 60. This projection has rounded edges 58 and extends downward from the lower surface of the wedge shaped plate 42. The preferred embodiment consists of a projection which is doughnut shaped 60, with a smaller neck 62 containing one radius, and a bulging protrusion 64 containing another radius. The doughnut shaped projection allows for range of motion. When the prosthesis is assembled, the projection 60 will then rest inside the female portion 12.

Alternatively, the projection on the male component can have straight cylindrical side walls with a rounded top (see FIG. 5). As with the previously described embodiment, the top of the projection will have a radius such that it will rest inside the female portion and allow for a range of motion.

The female portion 12 of the prosthesis comprises a cylindrical support plate 50, which is preferably flat. The plate 50 preferably has one rough-faced surface 44 that would mate with a vertebra. In a preferred embodiment, the female component is the lower component (see FIG. 1), and the rough surface 44 is on the lower surface of the support plate 78. The rough surface allows for another means of fixation to a vertebra, as an alternative to or in addition to the mechanical attachment elements. A presently preferred embodiment has both attachment elements, such as screws 14, and a rough surface 44 to provide for the most stable fixation.

The female component has at least one flange 16 extending vertically from the edge of the of the support plate. In a particularly preferred embodiment, the female component is the lower component and the flange extends downward from the edge of the lower surface of the support plate 78 (see FIG. 1). The flange is a mounting tab that can receive attachment elements, such as screws 14. The screws are guided through openings 22 in the flange in order to attach the female portion 12 to a vertebra. There are at least two openings through which at least two attachment elements can pass. In a preferred embodiment the openings 22 in the flange 16 are figure eight shaped openings 34 and have mouth sections (see FIG. 3). The figure eight shaped opening aids in facilitating different screw heights. The opening 22 can also be circular, or oval in shape.

In an alternative embodiment, there are two flanges 70 extending vertically from the plate (see FIG. 5). Each flange has at least one opening 22 for an attachment element to pass through.

Also, the female component has an additional opening 46 for attachment to a vertebra (see FIG. 5). This opening 46 extends through the end of the flange nearest the plate 98. The opening 46 is angled so that an attachment element, such as a screw 74, can be inserted into the vertebra through the opening at an angle. The opening is also recessed at the lower end 76 to receive the head of the screw, which is at an angle.

The female component further comprises a cylindrical concavity in the form of a cup shaped pocket 54. The cup shaped pocket extends Lip from the upper surface of the flat plate 52. The cup shaped opening 54 is adapted to receive the rounded projection of the male portion 60. The rounded edges 58 of the male projection rest inside the pocket of the female component. The pocket is designed with angled side walls 56. The angled side walls allow the male portion 10 to center itself within the pocket as the male portion 10 tilts in any direction.

In the preferred embodiments shown, the angled side walls 56 are straight. It is particularly preferred to have the angled side walls be substantially straight so that the rounded male projection can easily slide within the cup shaped opening to center itself. However, the angled side walls could be somewhat inwardly curving or concave without having a substantial adverse impact on centering. What is important is that the angled side walls, if they are curved, have a radius of curvature significantly larger than that of the rounded male projection where it contacts the side walls.

In an alternative embodiment, the side walls 56 are coated with or have overlying them an insert of a material that helps reduce friction between the two components. The coating or insert can be made of plastic or ceramic.

In the preferred embodiments, when the two components 10, 12 are placed together (see FIG. 1) the rounded projection 60 of the male component 10 fits into the cup shaped pocket 54 of the female component 12. The male component 10 then lies partly in the cylindrical pocket. As the male component goes through ranges of motion, the angled walls 56 of the female component 12 center the male component with the female component. The ranges of motion allowed around a spinal disk by human anatomy are approximately 15 degrees of flexion, 5 degrees of extension, 1 degree of rotation and 5 degrees of lateral bending. The prosthesis of the present invention is capable of those ranges of motion or more. Thus, the prosthesis is capable of the normal range of motion and it should be the anatomy of the motion segment itself that imposes constraints on ranges of motion.

The components 10, 12 of the system are preferably made of a metal alloy or ceramic material which is physiologically compatible with the vertebrae. The two components can also be made of dissimilar materials from each other. However, metal to metal contact allows for strength in the prosthesis. A particularly preferred embodiment is made from chromium cobalt alloy, but one skilled in the art would realize other possible materials or composites could be used that would be adequate to provide similar compatibility and strength. The attachment elements come in various lengths and diameters to accommodate the size of the prosthesis, which may vary due to the variation of human anatomy.

Another embodiment of the present invention is illustrated at FIGS. 6 and 7a–c. As with the previous embodiments, a female component 12 is provided. The female component includes a support plate 78 from which a flange 16 extends to aid in fastening the component to the appropriate vertebra. The lower surface 44 of the support plate is roughened to further aid in fixation of the plate to the vertebra. A cup shaped pocket 54 is provided with angled side walls 56 and a flat bottom 57.

While the female component is basically the same as the previous embodiments, a male component 110 is modified somewhat. Like the previous embodiments it includes a wedge shaped support plate 118 with a rough upper surface 180 which aids in fixation of the support plate to the appropriate vertebra. It also includes a flange 116 through which screws or other fasteners can be used to fix the component to the vertebra. However, a doughnut shaped articulating surface 160 is modified from the previous embodiments in that it includes a concave generally hemispheric bearing surface 181 that is preferably centered on the lower end of the doughnut shaped surface.

Figure 7A:
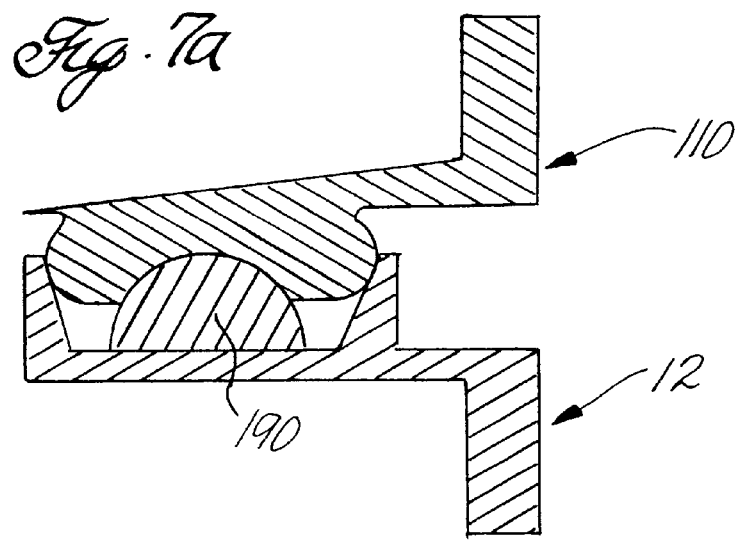
FIGS. 7a–c are side views in section of the embodiment of FIG. 6 illustrating the flexion and extension of the device.
Figure 7B:
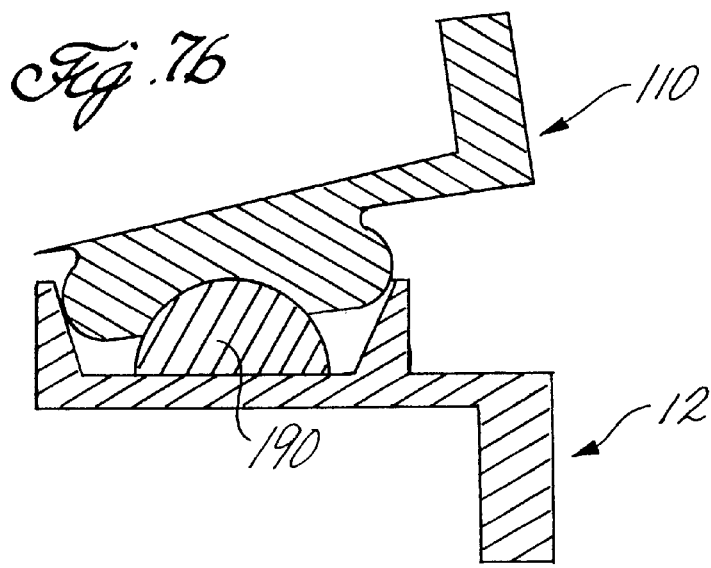
Figure 7C:
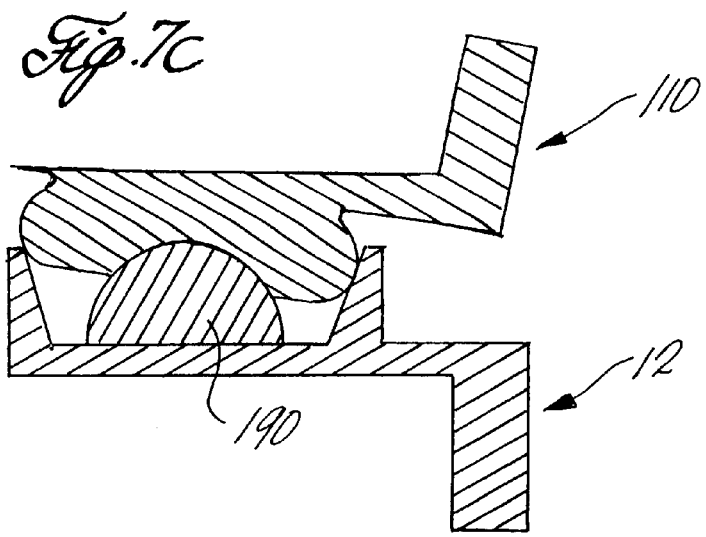

This embodiment also includes a third component, a generally hemispheric bearing 190. The hemispheric bearing includes a flat lower bearing surface 192 and a convex hemispheric upper bearing surface 194. The hemispheric bearing is useful in distributing the load borne by the device over a broader area so as to reduce wear. The relationship between the hemispheric bearing and the male and female components is best illustrated in FIGS. 7a–c. According to FIG. 7a, the device is illustrated as implanted in a patient whose spine is in a normal resting position. The male component 110 is centered above the female component 12 as is the hemispheric bearing 190. When the device is in this position, the patient's spine is basically straight with a slight amount of lordosis provided by the wedge shaped support plate.

In FIG. 7b, the device is illustrated with the patient's spine in a state of extension. The male component is still centered above the female component with the doughnut shaped articulating surface of the male component engaged with the cup shaped pocket of the female component. However, when the male and female components are extended with respect to one another, the hemispheric bearing slides ventrally along the flat bottom of the cup shaped pocket of the female component. It should be recognized that the concave bearing surface of the male component and the convex bearing surface of the hemispheric bearing remain in contact throughout flexion and extension so that a significant portion of the load borne by the male component is transferred to the hemispheric bearing. Likewise, the load transferred to the hemispheric bearing is transferred to the female component as the lower bearing surface of the hemispheric bearing remains in contact with the flat surface of the cup shaped pocket of the female component.

As illustrated in FIG. 7c, when the patient's spine is in a state of flexion, the various bearing surfaces remain in contact with one another as the hemispheric bearing slides dorsally. Even though the hemispheric bearing slides, the male component remains centered over the female component. Without the hemispheric bearing, the entire load would be transferred from the male component to the female component over the small surface area of the doughnut shaped articulating surface which directly contacts the cup shaped pocket of the female component. The use of the device as modified to include a hemispheric bearing helps to avoid premature wear of the prosthesis by distributing the loads borne by the articulating joint formed by the device over a larger surface area. Moreover, to the extent the surfaces wear, the device tends to retain its self-centering properties as the components tend to wear evenly.

While flexion and extension of the device are illustrated, it should be apparent that lateral bending is also permitted with a lateral sliding of the hemispheric bearing along the cup shaped pocket of the female component. Again, as with flexion and extension, during lateral bending the male component remains centered over the female component while the hemispheric bearing slides from side to side within the cup shaped pocket.

In the preferred embodiment, the hemispheric bearing is made of materials compatible with the male and female components. Examples of materials include biologically compatible metal alloys or ceramics. The various bearing, surfaces may also include low friction coatings that are biologically compatible.

The foregoing describes the system and how its components are interrelated. An example of a typical installation sequence for the system will now be described.

The approach to the surgery can be either the standard anterior transabdominal or retroperiteal approach. The first step in the sequence is resection of the disk so that the resection is 1.5 inches wide and 1.5 inches deep. There must be as much of the anterior longitudinal ligament left as possible on either side of the diskectomy. The next step is to denude the adjacent vertebral surfaces to bleeding bone, and then distract the adjacent vertebrae with a distracter chosen by the surgeon or with a triple arthrodesis distracter. After those steps are complete, anterior-posterior and lateral x-rays are obtained to determine that the motion segment is distracted to a reasonable height and still in alignment. Then, the distraction is measured. An ideal distraction is about 18 mm. The prosthesis is then assembled and inserted between the vertebrae. After the prosthesis is inserted, cancellous screws are inserted through the flanges in the prosthesis to the vertebral bodies about and below the prosthesis. Final x-rays are taken and the wound is closed in a routine manner.

The preceding description indicates the preferred embodiments of the present invention, but it is not limited to the designs shown. Therefore, the present invention is not intended to be limited to the working embodiments described above. The scope of the invention is defined in the following claims.

What is claimed is:

1. An intervertebral prosthetic disk comprising:
   a male component comprising a first support plate, a first attachment element allowing fixation to a vertebra, and an articulating projection, the articulating projection defining a concave lower bearing surface;
   a female component comprising a second support plate, a second attachment element allowing fixation to a vertebra, and a circular pocket with a flat bottom bearing surface having a first diameter and angled walls suitable for receiving the articulating projection; and
   a bearing comprising a convex upper bearing surface adapted to engage the concave bearing surface of the male component and a flat lower bearing surface with a second diameter smaller than the first diameter of the flat bottom bearing surface of the female component adapted to engage the flat bottom bearing surface of the female component.

2. The prosthetic disk of claim 1, wherein the first and second attachment elements each comprise at least one vertical flange extending from the support plate and contain at least one opening through which a mechanical attachment element can pass.

3. The prosthetic disk of claim 2, wherein the mechanical attachment element is selected from the group consisting of screws, pegs and rods.

4. The prosthetic disk of claim 3 wherein for both the male and female components, the number of openings and mechanical attachment elements is at least two.

5. The prosthetic disk of claim 1, wherein each of the first and second attachment elements comprises a porous coating for permanent bony fixation on a bone-facing surface of the respective support plate.

6. The prosthetic disk of claim 1, wherein the first and second attachment elements each comprise at least one flange, at least one mechanical attachment element, and a porous coating on a bone-facing surface of the respective support plate.

7. The prosthetic disk in claim 1, wherein the first support plate is wedge shaped to facilitate building lordosis.

8. The prosthetic disk of claim 1, wherein at least one of the components is made of a material selected from the group consisting of ceramics and metal alloys.

9. The prosthetic disk of claim 1, wherein the articulating projection is doughnut shaped to facilitate range of motion.

10. The prosthetic disk of claim 7 wherein the wedge shaped plate defines a recessed, angled hole through which an attachment element can pass.

11. The prosthetic disk of claim 10 wherein the attachment element is a screw.

12. The prosthetic disk of claim 1 wherein the second support plate comprises a recessed, angled hole through which an attachment element can pass.

13. The prosthetic disk of claim 12 wherein the attachment element is a screw.

14. An intervertebral prosthetic disk comprising:
   a male component comprising an articulating projection with a double radius and a concave bearing surface;
   a bearing comprising a convex upper surface for engagement with the concave bearing surface of the male component and a lower surface opposite the upper surface; and
   a female component comprising a pocket adapted to receive the articulating projection of the male component and the lower surface of the bearing so that the bearing is laterally moveable within the pocket.

15. An intervertebral prosthetic disk recited in claim 14 wherein a coating or insert is provided on the inside surface of the pocket.

16. The intervertebral prosthetic disk recited in claim 14 wherein the bearing is of a generally hemispheric shape.

17. An prosthetic disk for insertion between first and second adjacent vertebrae comprising:
   a first component comprising a first plate for fixation to the first vertebra and a rounded projection extending from the first plate away from the first vertebra, the projection defining a concave bearing surface distal the first plate;

a bearing comprising a convex surface for engagement with the concave bearing surface of the first component and a generally flat surface having a first diameter opposite the convex surface; and a second component comprising a second plate for fixation to the second vertebra and a cup extending from the second plate away from the second vertebra, the cup defining an angled circular side wall for engagement with the rounded projection and a generally flat lower surface having a second diameter greater than the first diameter of the bearing for engaging the generally flat surface of the bearing so that the bearing is laterally moveable on the flat lower surface of the cup.

18. The prosthetic disk recited in claim 17 wherein the bearing is of a generally hemispheric shape.

19. The prosthetic disk recited in claim 17 wherein one of the first and second plates is wedge shaped.

20. The prosthetic disk recited in claim 17 wherein each of the first and second plates further includes a flange to assist in fixing the plate to the respective vertebra.

21. An intervertebral prosthetic disk comprising:

a male component comprising a first support plate, a first attachment element allowing fixation to a vertebra, and an articulating projection, the articulating projection defining a concave lower bearing surface;

a female component comprising a second support plate, a second attachment element allowing fixation to a vertebra, and a circular pocket with a flat bottom bearing surface and angled walls suitable for receiving the articulating projection; and a bearing comprising a convex upper bearing surface adapted to engage the concave bearing surface of the male component and a flat lower bearing surface adapted to engage the flat bottom bearing surface of the female component;

wherein the articulating projection of the male component is supported both on the walls of the circular pocket of the female component and on the convex upper bearing surface of the bearing; and wherein movement occurs between the articulating projection of the male component and the circular pocket of the female component, between the convex upper surface of the bearing and the concave lower bearing surface of the articulating projection, and through movement of the bearing within the pocket.

22. An intervertebral prosthetic disk comprising:

a male component comprising an articulating projection with a double radius and a concave bearing surface;

a bearing comprising a convex upper surface for engagement with the concave bearing surface of the male component and a lower surface opposite the upper surface; and a female component comprising a pocket adapted to receive the articulating projection of the male component and the lower surface of the bearing;

wherein the articulating projection of the male component is supported both on the walls of the pocket of the female component and on the convex upper surface of the bearing and movement occurs between the articulating projection of the male component and the pocket of the female component, between the convex upper surface of the bearing and the concave lower bearing surface of the articulating projection, and through movement of the bearing within the pocket.

* * * * *